(12) United States Patent
Ahari et al.

(10) Patent No.: US 11,154,281 B1
(45) Date of Patent: Oct. 26, 2021

(54) SEALANT PLUG DELIVERY SYSTEM AND METHOD OF USE

(71) Applicant: Med-Genesis, LLC, Clearwater, FL (US)

(72) Inventors: Frederick Ahari, Belleair Beach, FL (US); John S. Fisher, Belleair, FL (US); Jon Frederick Roever, Ocala, FL (US)

(73) Assignee: Med-Genesis, LLC, Clearwater, FL (US)

( * ) Notice: Subject to any disclaimer, the term of this patent is extended or adjusted under 35 U.S.C. 154(b) by 0 days.

(21) Appl. No.: 17/229,079

(22) Filed: Apr. 13, 2021

(51) Int. Cl.
*A61B 10/02* (2006.01)
(52) U.S. Cl.
CPC ...... *A61B 10/0266* (2013.01); *A61B 10/0283* (2013.01)
(58) Field of Classification Search
CPC .................. A61B 10/0266; A61B 10/0283
See application file for complete search history.

(56) References Cited

U.S. PATENT DOCUMENTS

| | | | | |
|---|---|---|---|---|
| 4,105,030 A | * | 8/1978 | Kercso | A61M 37/0069 604/506 |
| 4,661,103 A | * | 4/1987 | Harman | A61M 37/0069 221/186 |
| 5,273,532 A | * | 12/1993 | Niezink | A61M 37/0069 604/60 |
| 6,592,608 B2 | | 7/2003 | Fisher et al. | |
| 6,685,727 B2 | | 2/2004 | Fisher et al. | |
| 6,790,185 B1 | | 9/2004 | Fisher et al. | |
| 6,840,952 B2 | * | 1/2005 | Saker | A61B 17/00491 604/187 |
| 7,001,410 B2 | | 2/2006 | Fisher et al. | |
| 7,329,414 B2 | | 2/2008 | Fisher et al. | |
| 10,213,555 B1 | * | 2/2019 | Carranza | A61M 5/31585 |
| 2004/0127765 A1 | * | 7/2004 | Seiler | A61N 5/1007 600/7 |
| 2013/0253402 A1 | * | 9/2013 | Badawi | A61F 9/00781 604/8 |
| 2015/0045665 A1 | * | 2/2015 | Lau | A61M 25/0084 600/431 |

* cited by examiner

*Primary Examiner* — Rene T Towa
(74) *Attorney, Agent, or Firm* — Nicholas Pfeifer; Smith & Hopen, P.A.

(57) ABSTRACT

A plug delivery system and method of use. The plug delivery device includes a support leg, a plunger, and an extractor. The support leg includes an internal receiving space configured to receive an implanted coaxial needle assembly through an opening in the distal end. The plunger extends at least partially through the internal receiving space of the support leg and has a longitudinally adjustable relation with respect to the support leg. The extractor is also configured to translate in a longitudinal direction with respect to the support leg and has a needle connection component configured to engage the coaxial needle assembly. The extractor can be moved distally in the longitudinal direction to engage the coaxial needle assembly and then moved distally to concurrently retract the coaxial needle assembly while the plunger remains relatively stationary to deploy the sealant plug residing in the coaxial needle assembly.

20 Claims, 13 Drawing Sheets

SEALANT PLUG DELIVERY SYSTEM AND METHOD OF USE

BACKGROUND OF THE INVENTION

1. Field of the Invention

This invention relates, generally, to medical arts. More particularly, it relates to system and method for sealing openings in a mammalian body.

2. Brief Description of the Prior Art

Numerous medical procedures and even non-medical events can result in openings in the body that need to be sealed to stop bodily fluids and/or gaseous fluids from exiting the body. For example, sealing means for closing openings are needed to stop the flow of blood, cerebral spinal fluid, air, and other fluids. These sealing means are particularly important when it comes to stopping the flow of fluids from organs.

For exemplary purposes, consider an opening made by a biopsy needle. In a biopsy procedure, a biopsy needle adapted to collect tissue is inserted into a suspected lesion, usually multiple times. When a sufficient quantity of the lesion has been collected, the samples are taken to a lab for analysis. To perform the procedure, a coaxial needle first punctures the body/tissue and inserted so that its leading/distal end is positioned near the suspected lesion. The biopsy needle is then inserted through the coaxial needle and samples are collected.

The puncture opening made by the coaxial needle may close and heal naturally if the lesion is in soft tissue such as a breast. However, if a lesion is in the lung or any other internal organs, the puncture opening made by the coaxial needle may need to be closed quickly. In fact, air leaks ("pneumothorax") commonly occur at pulmonary tissue sites that have been biopsied or dissected during surgical resection and manipulation.

Obviously, an opening in a lung is undesirable because air can leak therefrom and cause the lung to collapse. In fact, it is estimated that pneumothorax occurs in about thirty per cent (30%) of lung biopsies. Openings in other organs, such as the heart, liver, kidney, and the like are also undesirable due to excess bleeding and other related problems.

Existing bioabsorbable sealant plugs and delivery methods, such as those in U.S. Pat. Nos. 6,790,185; 7,001,410; 6,685,727; 6,592,608; and 7,329,414 to the same inventors have been proven to be beneficial in reducing pneumothorax. However, pneumothorax still occurred in about 30% of lung biopsies in which these patented plugs and methods were used. One reason for the significant number of pneumothorax occurrences is associated with the delivery system used to deliver the plug within the biopsy track within the pleura.

Existing delivery systems can be complicated to use and require precise measurements attained through medical imaging to ensure that the plug is delivered in the correct location. For example, as explained in U.S. Pat. No. 6,790,185, after a conventional biopsy procedure has been performed, "a predetermined distance is added to distance 'a' to produce a distance 'd' and coaxial needle 14 is either advanced in the direction of directional arrow 32 or retracted in the direction of arrow 34 so that its distal end is distance 'd' from the surface of the patient's skin. Holder 28 is positioned on a graduation mark on the coaxial needle that represents said distance 'd' and holder 28 is placed into abutting relation to the patient's skin, thereby positioning distal end 14 of the coaxial needle at the desired depth as depicted in FIG. 5B.

The predetermined distance is 0.5 cm less than the length of the sealant plug, in centimeters. Thus, where a sealant plug is 2.5 cm in length and where distance 'a' is 2.0 cm, holder 28 is slid along the length of coaxial needle 14 until said holder is positioned at the 4.0 cm graduation markers as depicted in FIG. 5B and said holder is placed flush with the patient's skin. This positions the distal (leading) end of coaxial needle 14 four centimeters (4.0 cm) below the surface of the patient's skin and 2.0 cm below the surface of the internal organ. As will become clear as this description proceeds, a sealant plug is introduced into the lumen of coaxial needle 14 and is pushed until its leading end is substantially flush with distal end 14 of the coaxial needle. The sealant plug stays in place when the coaxial needle is withdrawn, the therefore the leading end of the sealant plug will remain in the biopsy tract in the internal organ, but the trailing end of the sealant plug will extend or protrude from the surface of the internal organ by about 0.5 centimeters.

The next step, as best understood in connection with FIG. 6, requires that supporting leg 36 and plunger 38 be assembled as indicated and adjusted in accordance with a chart, depicted in FIG. 6A, that is provided to the end user, said chart being provided as a part of a package including instructions for use of the novel tool. The chart provides the plunger-to-supporting leg ratio with respect to measurement of distance 'a.' Graduation markings in centimeters are provided along the extent of supporting leg 36 and plunger 38."

As explained, the user of the prior art device needs to know the distance between the patient's skin and pleura and then needs to properly lock the location of the plunger relative to the legs to ensure that the plug is deposited at the right location. The process is so complicated that a chart is required to help determine the proper locking location of the plunger.

Accordingly, what is needed is an improved plug delivery system and method of use that is substantially easier to use and less prone to human error. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved plug delivery system and method of use that is substantially easier to use and less prone to human error is now met by a new, useful, and nonobvious invention.

The sealant plug delivery system of the present invention includes a plug delivery device configured to deploy a sealant plug from an internal lumen of a coaxial needle assembly. In some embodiments, the coaxial needle assembly includes a plug housing in which the sealant plug initially resides prior to the plunger forcing the sealant plug towards the distal end of the coaxial needle.

The plug delivery device includes a support leg, a plunger rod (a.k.a. a "plunger"), and an extractor. In some embodiments, the support leg incudes a proximal end, a distal end, and an elongated body extending therebetween. The elongated body includes an internal receiving space configured to receive the coaxial needle assembly through an opening in the distal end.

The plunger rod extends at least partially through the internal receiving space of the support leg and includes a cross-sectional area smaller than a cross-sectional area of the internal lumen of the coaxial needle assembly. Moreover, the plunger rod has a longitudinally adjustable relation with respect to the support leg.

The extractor is also configured to translate in a longitudinal direction with respect to the support leg and has a needle connection component configured to engage the coaxial needle assembly. The extractor further includes a locked configuration and an unlocked configuration. In the locked configuration, the extractor moves concurrently with the plunger rod in the longitudinal direction. In the unlocked position, the extractor can move relative to the plunger rod in the longitudinal direction. As a result, the extractor can be moved distally in the longitudinal direction to engage the coaxial needle assembly and, while in the unlocked position, the extractor can be translationally retracted to concurrently retract the coaxial needle assembly while the plunger remains relatively stationary to deploy the sealant plug residing in the coaxial needle assembly.

Some embodiments include the coaxial needle assembly having a length that is equal to or greater than a distance between the distal end of the plunger and the needle connection component of the extractor when the extractor is in the locked configuration. Some embodiments include the coaxial needle assembly having a first length that is equal to or greater than an ensleeved section of the plunger when the extractor is connected to the coaxial needle assembly.

In some embodiments, an extraction handle is in operable communication the extractor. As a result, translation of the extraction handle causes the extractor to translate at least when the extractor is in the unlocked position.

Some embodiments further include an extraction slot disposed in a lateral surface of the support leg. The extraction slot has a length extending in a longitudinal direction and is configured to receive the extraction handle.

Some embodiments further include a pusher component configured to translate in the longitudinal direction relative to the support leg. The pusher component includes a lumen configured to receive the extractor, an extraction channel laterally aligned with the extraction slot in the support leg, and a locking passage into which the extraction handle can be rotated to move the extractor into the locked position. The extraction channel extends in the longitudinal direction and is configured to receive the extraction handle. Some embodiments further include a translation actuator configured to translate the pusher component when actuated.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, "biocompatible" means bioabsorbable, biodegradable, or resorbable.

While openings in a mammalian body may be formed by numerous other medical procedures and non-medical events, the figures and this detailed description of the invention focus on using the present invention to deploy a biocompatible plug at least partially within a biopsy tract in the pleura of a patient. However, the focus on a biopsy procedure is for exemplary purposes. Furthermore, while the exemplary biopsy site is located within a patient's lung, it should be understood that the utility of this invention is not restricted to sealing openings formed in lungs by biopsy procedures. Rather, it should be understood that this invention may be used to seal openings formed by any means in organs, such as the heart, brain, liver, spinal cord, and kidneys, and even in hard tissue such as bone, cartilage, and the like.

The present invention includes a simpler and more efficient plug delivery system and method of use. The present invention is used to deliver a plug within a patient as a coaxial needle is removed from the body of the patient without having to first determine and set the location of the plunger rod relative to the support leg of the device based on the depth of the coaxial needle in the patient. Removing these steps creates a much simpler method of deploying a sealant plug and eliminates the possibility of human error associated with incorrectly determining and setting the location of the plunger rod relative to the support leg of the device based on the depth of the coaxial needle within the patient. Accordingly, the present invention is a simpler and safer plug delivery system and method of use.

Figure 1:
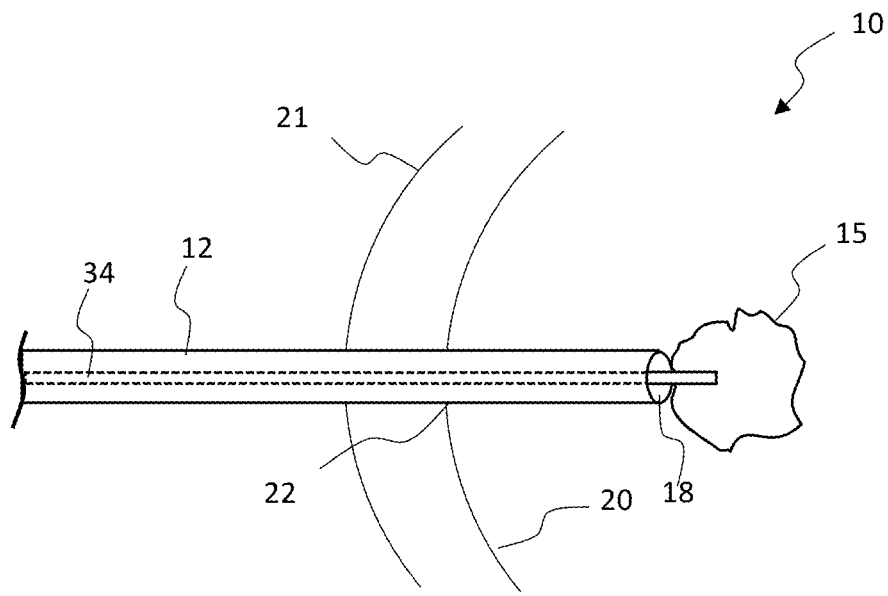
FIG. 1 is a diagram illustrating a coaxial needle at a surgical depth proximate to tissue being sampled in a biopsy procedure.

Referring to FIG. 1, it will there be seen that the reference numeral 10 denotes a biopsy site as a whole, in which cellular material is being retrieved from lesion 15 within a patient's lung. Specifically, coaxial needle 12 has been inserted through the patient's skin 21 and pleura 20 and distal end 14 of coaxial needle 12 has been moved to a position adjacent to lesion 15. Biopsy needle 34 has been inserted through lumen 18 of coaxial needle 12 and is used to extract cellular material from lesion 15.

Figure 2:
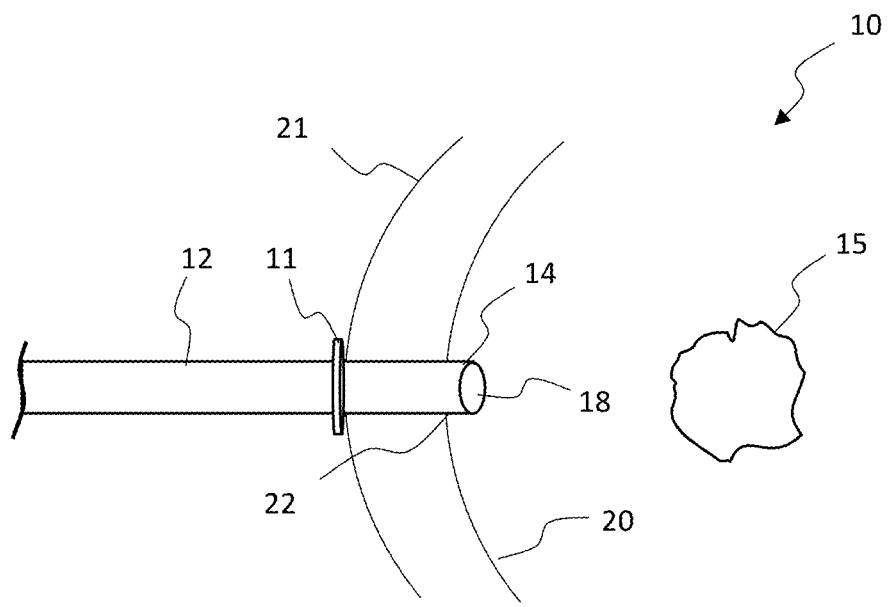
FIG. 2 is a diagram illustrating a coaxial needle secured at an exemplary plug deployment depth.

Following the procedure for retrieving cellular material from lesion 15, biopsy needle 34 is withdrawn from lumen 18 of coaxial needle 12 and the cellular material is delivered to a lab for analysis. The biopsy needle is not used again in the procedure because the biopsy procedure has been concluded. Coaxial needle 12 is then retracted and secured at a plug deployment depth as shown in FIG. 2. The only remaining task is to seal biopsy tract 22 (also generally referred to as "passage 22") within pleura 20 via a sealant plug (also generally referred to as "the plug") delivered to a precise location within biopsy tract 22. This task may be performed using plug deployment device 40 as will be explained in subsequent sections.

Figure 3:
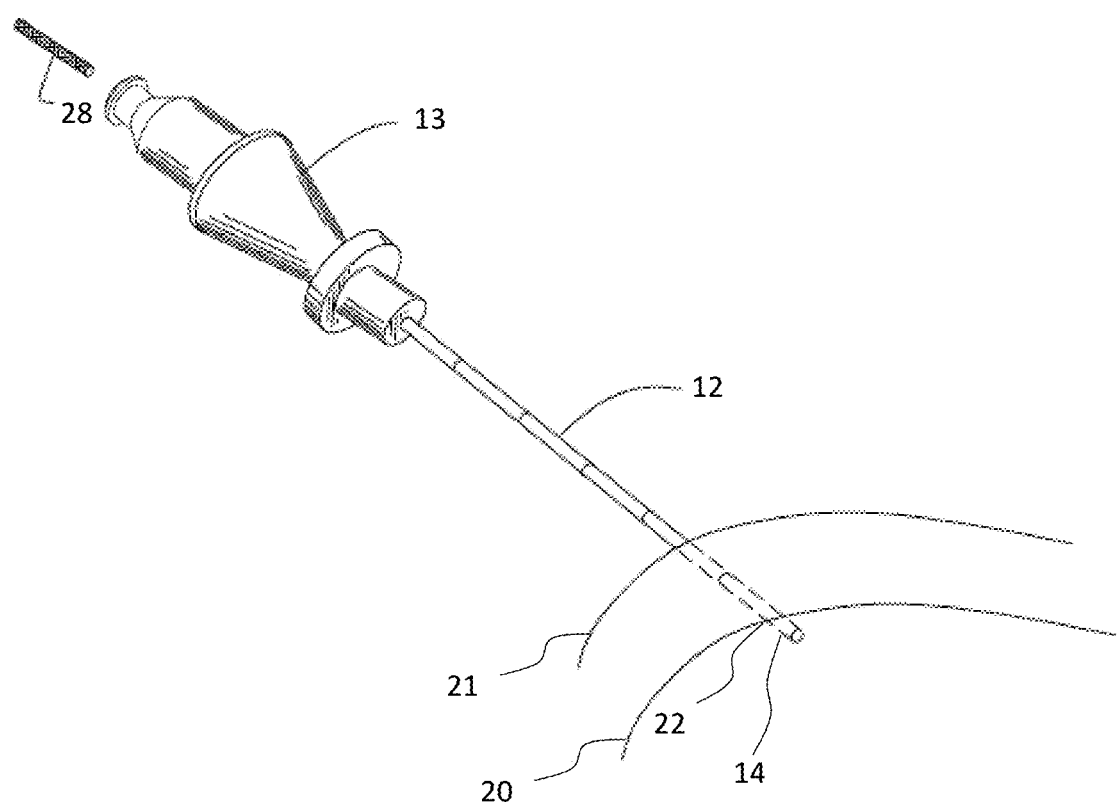
FIG. 3 is a perspective view of an embodiment of the coaxial needle assembly having penetrated a patient's skin and pleura.

An exemplary plug is depicted in FIG. 3 and identified via reference numeral 28. Plug 28 may be comprised of a material that expands upon contact with a stimulant such as water, blood, air, visible light, or other electromagnetic radiation such as a laser beam, a preselected chemical, and so on. In a preferred embodiment, the stimulant is moisture which is naturally present on the surface of a patient's lungs or other soft tissue, internal organs, or the like. Thus, some embodiments of plug 28 have a dehydrated (i.e., contracted) state or partially dehydrated state and a hydrated (i.e., expanded) state. Plug 28 is preferably configured to expand and seal passage 22 almost immediately to prevent unnecessary fluid loss through passage 22.

In some embodiments, plug 28 is generally a solid cylindrical shape to easily pass through coaxial needle 12. In addition, plug 28 has a sufficient length to extend both inside and outside of pleura 20. In some embodiments, plug 28 has an elongated body that is not necessarily cylindrical. Moreover, plug 28 may have any cross-sectional shape, but preferably has a length sufficient to extend both inside and outside of pleura 20.

In some embodiments, plug 28 is roughly 2.5 cm in length in a dehydrated state and roughly 2 cm remains within pleura 20 and roughly 0.5 cm remains external to pleura 20 when plug 28 is in its inserted location. In some embodiments, plug 28 is roughly 3 cm in length in a dehydrated state and roughly 2 cm remains within pleura 20 and roughly 1 cm remains external to pleura 20 when plug 28 is in its inserted location. In some embodiments, the inserted location includes at least 0.5 cm extending internally or externally with respect to pleura 20. As a result of the need to deploy plug 28 within pleura 20, the plug deployment depth of coaxial needle 12 will correspond to plug 28 length, which will be explained in greater detail below.

In the dehydrated state, plug 28 has a cross-sectional area sufficient to allow plug 28 to pass through lumen 18 in coaxial needle 12. The hydrated state includes plug 28 having an expanded cross-sectional area that is greater than the cross-sectional area of lumen 18 and passage 22. Plug 28 further includes various cross-sectional sizes during expansion that are larger than the cross-sectional size when dehydrated and smaller than the cross-sectional size when fully hydrated.

Plug 28 is also biocompatible, i.e., it is formed of a bioabsorbable material so that it is bioabsorbed by the body as the opening heals. Since people heal at different rates, a bioabsorbable material should be selected so that it is fully bioabsorbed in a period of time such as a few days to a few months.

Plug 28 may be comprised of any suitable bioabsorbable materials that expand when contacted by aqueous fluids including, but not limited to hydrogels, collagen, polysalactic acid, and any other suitable hydrophilic agents. Additional compositions include polymers that swell in the presence of aqueous fluids. Virtually all of the following polymers are hydrogels. Synthetic hydrogels can be prepared from the following classes of polymers and these are generally considered to be non-biodegradable: poly(hydroxyalkyl methylacrylates), such as poly(glyceryl methacrylate), poly(acrylamide), and poly(methacrylamide) and derivatives, poly(N-vinyl-2-pyrrolidone) anionic and cationic hydrogelspoly(vinylalcohol)poly(ethylene glycol) diacrylate and derivatives from block copolymers composed of poly(ethylene oxide)-poly(propyleneoxide)-poly(ethyleneoxide) and poly(propyleneoxide)-poly(ethyleneoxide)-poly(propyleneoxide) blocks, respectively.

Biodegradable synthetic hydrogels can be prepared from polymers such as those listed above by incorporating one or more of the following monomers: glycolide, lactide, E-caprolactone, P-dioxanone, and trimethylene carbonate. In addition, biodegradable hydrogels can be based on natural products such as polypeprides such as gelatin which may be cross-linked with formaldehyde or glutaraldehyde and various other dialdehydes.

Some other optional compositions include modified chitin hydrogels, which may be prepared from partially N-deacetylated chitin and then cross-linked with agents such as glutaraldehyde; dextran, a polysaccharide, derivatized with groups such as 3-acryloyl-2-hydroxypropyl esters and subsequently cross-linked by free radical copolymerization with N',N'-methylenebisacrylamide; starch that is similarly derivatized; and glycidyl acrylate followed by free radical cross-linking as described above.

As previously stated, following the biopsy procedure, coaxial needle 12 is retracted from its biopsy location (a location in which distal end 14 of the coaxial needle is adjacent to the lesion) to a plug deployment depth exemplified in FIG. 2. The plug deployment depth includes distal end 14 of coaxial needle 12 residing internally with respect to pleura 20 or within passage 22. In some embodiments, the distance between distal end 14 and pleura 20 is not greater than the contracted length of plug 28. In some embodiments, the plug deployment depth includes distal end 14 of coaxial needle 12 residing between roughly 0.5 cm and 2 cm within pleura 20. In some embodiments, the distal end of the coaxial needle is between roughly 1 cm and 2 cm from the wall of the organ. These parameters ensure that plug 28 will be deployed at least partially within passage 22 to seal said passage.

In some embodiments, coaxial needle 12 includes a predetermined length residing between its distal end 14 and the proximal end of luer connector 13. This predetermined length ensures that the preassembled plug deployment device 40 and its corresponding plunger 42 will operate in conjunction to deploy plug 28 at the proper location relative to passage 22. These details will be explained more thoroughly in subsequent paragraphs.

The proximal end of luer connector 13 includes an opening for receiving plug 28. In addition, the proximal end of luer connector 13 includes male luer fitting 11, which is configured to engage female luer fitting 32 on plug housing 30 or on extractor 50 on plug deployment device 40, which will be discussed in greater below. While the depicted fitting at the proximal end of luer connector 13 is a male luer fitting, some embodiments use other connection components known in the art (referred to generally as "needle connection components"). Likewise, the corresponding fittings on plug housing 30 or on extractor 50 may be any other connection components known in the art to allow luer connector 13 to engage plug housing 30 or extractor 50.

Figure 4:
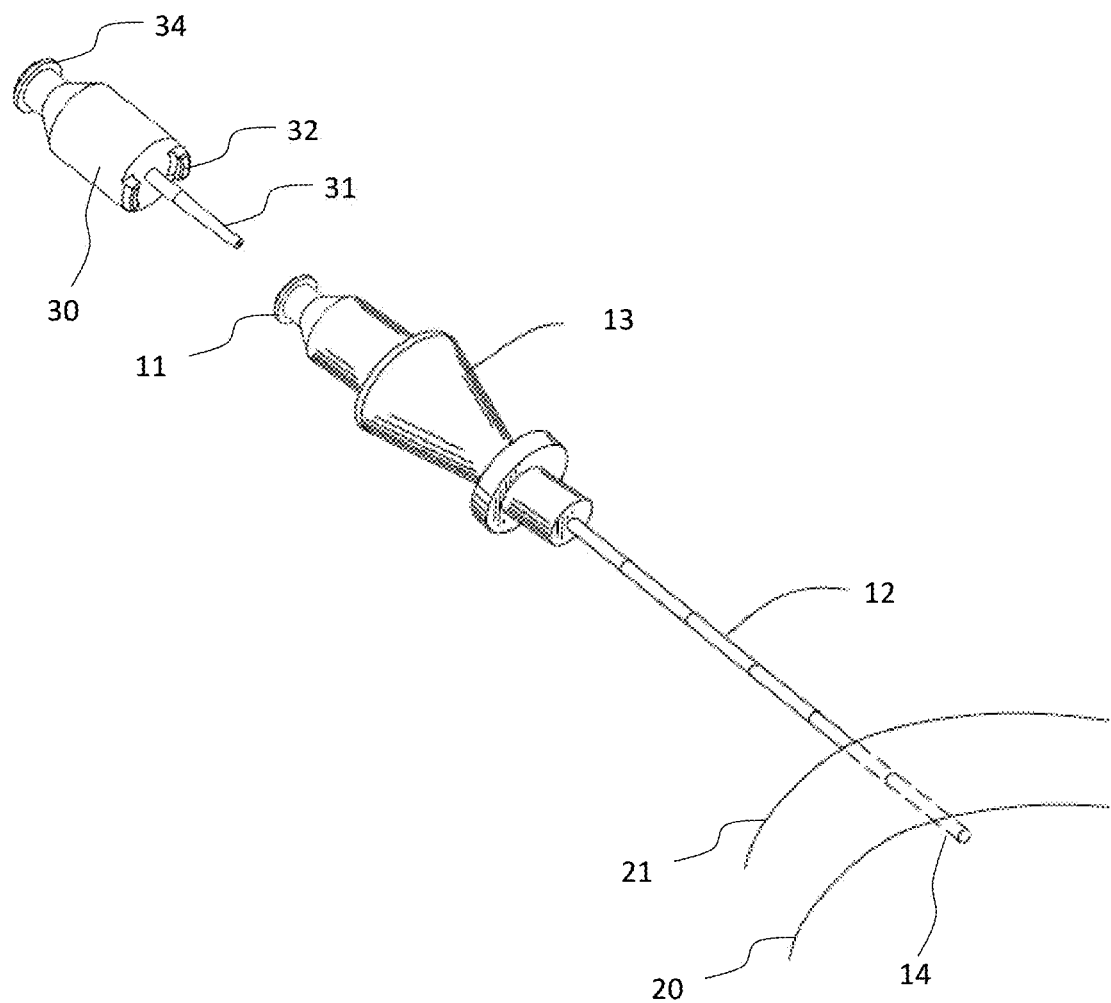
FIG. 4 is an exploded view of an embodiment of the coaxial needle assembly having penetrated a patient's skin and pleura.

In some embodiments, luer connector 13 is adapted to connect to plug housing 30, such as the one exemplified in FIG. 4. In such embodiments, the combined length of coaxial needle 12 and plug housing 30 is predetermined. This predetermined combined length ensures that the pre-assembled plug deployment device 40 and its corresponding plunger 42 will operate in conjunction to deploy plug 28 at the proper location relative to passage 22. Again, these details will be explained more thoroughly in subsequent paragraphs.

Plug housing 30 includes an internal lumen in which plug 28 may temporarily resides, preferably in a dehydrated or partially dehydrated state. Plug housing 30 can be secured to luer connector 13 and as a result plug 28 can be forced from plug housing 30 into coaxial needle 12. In some embodiments, plug housing 30 includes female luer fitting 32 configured to securely engage male fitting 11 on luer connector 13. However, alternative known mechanisms and methods may be used to connect plug housing 30 to luer connector 13.

Furthermore, plug housing 30 includes male luer fitting 34 at its proximal end. Male luer fitting 34 is configured to engage a female luer fitting on extractor 50 on plug deployment device 40 (see FIGS. 7, 8, and 11) which will be discussed in greater detail below. It should be noted that alternative known mechanisms and methods may be used to connect male luer fitting 34 to extractor 50.

Figure 5:
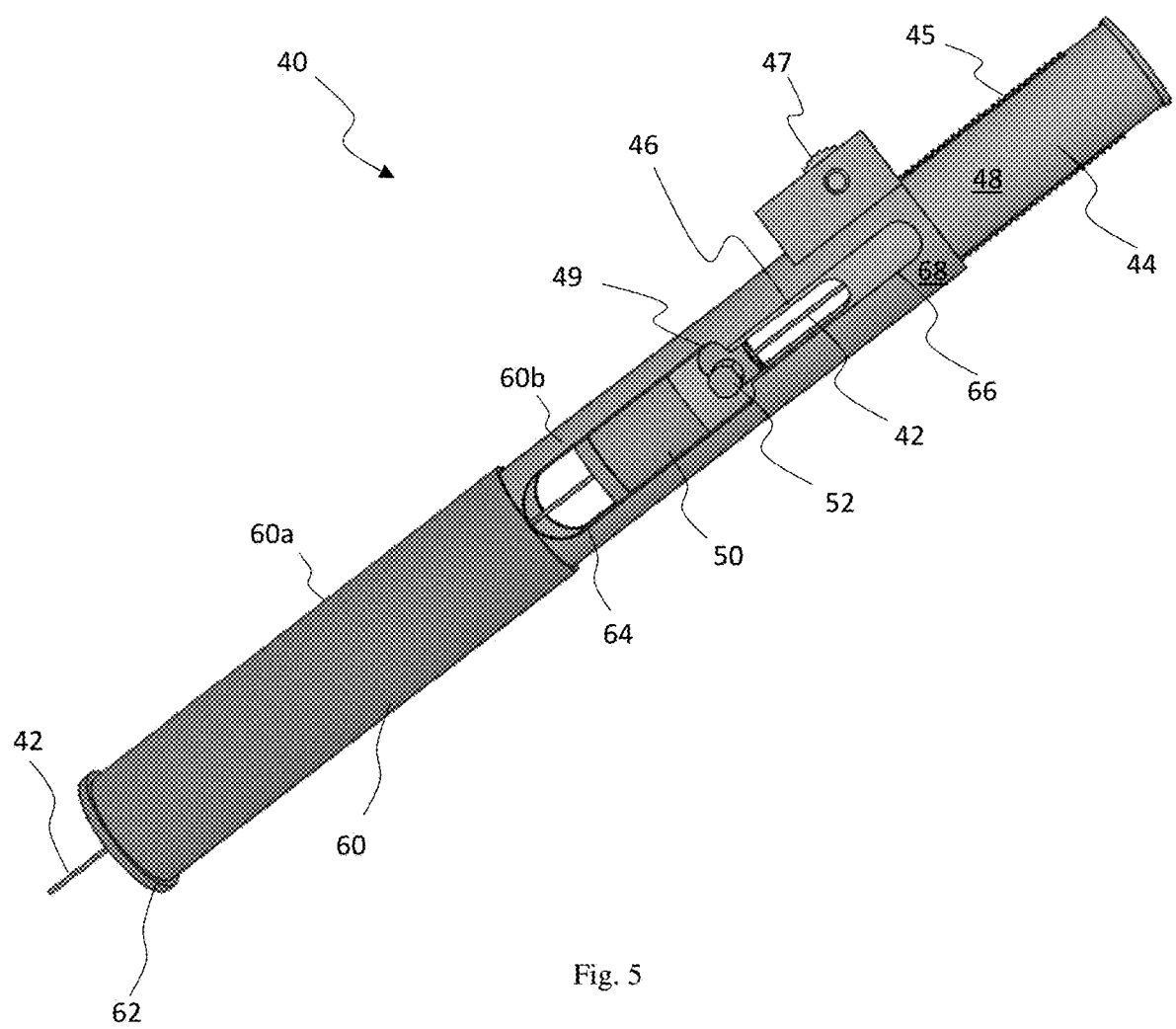
FIG. 5 is a perspective view of an embodiment of the plug deployment device.
Figure 6:
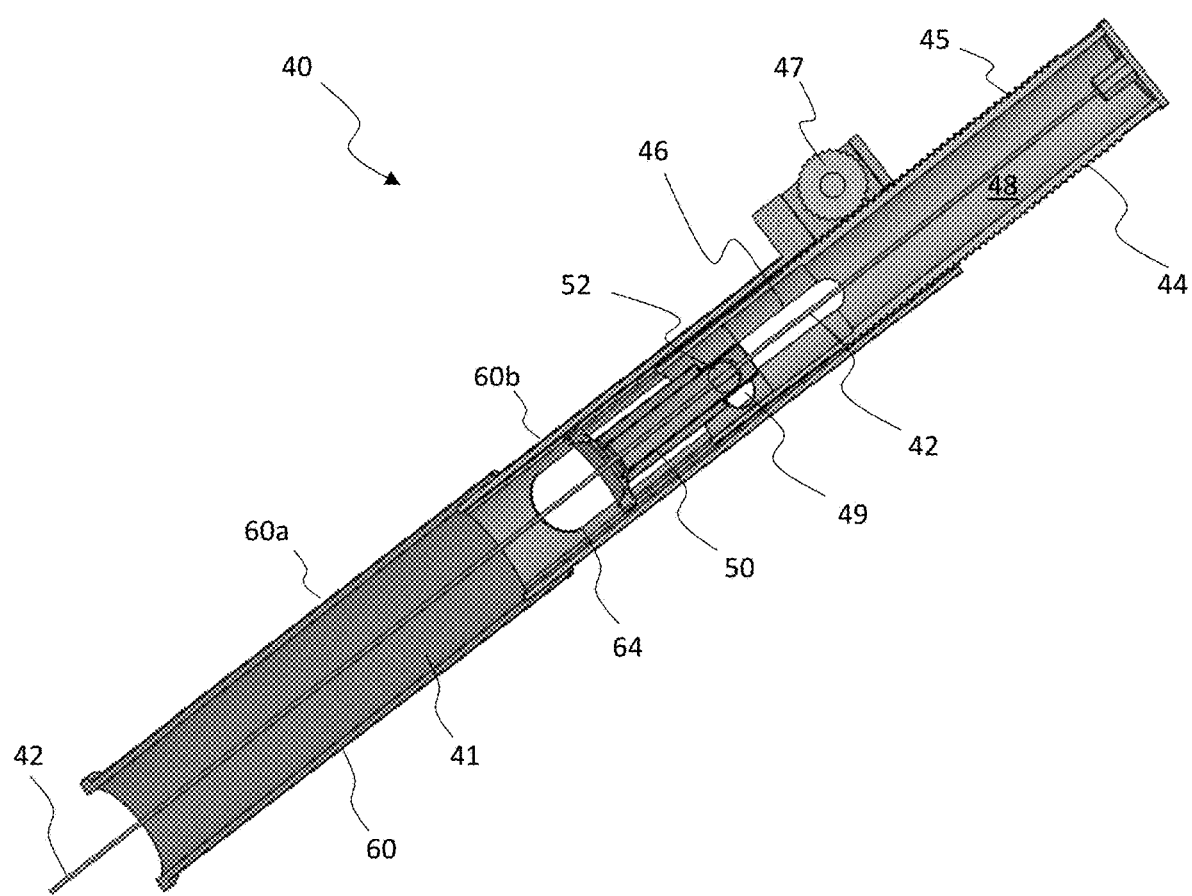
FIG. 6 is a cross-sectional view of an embodiment of the plug deployment device.
Figure 7:
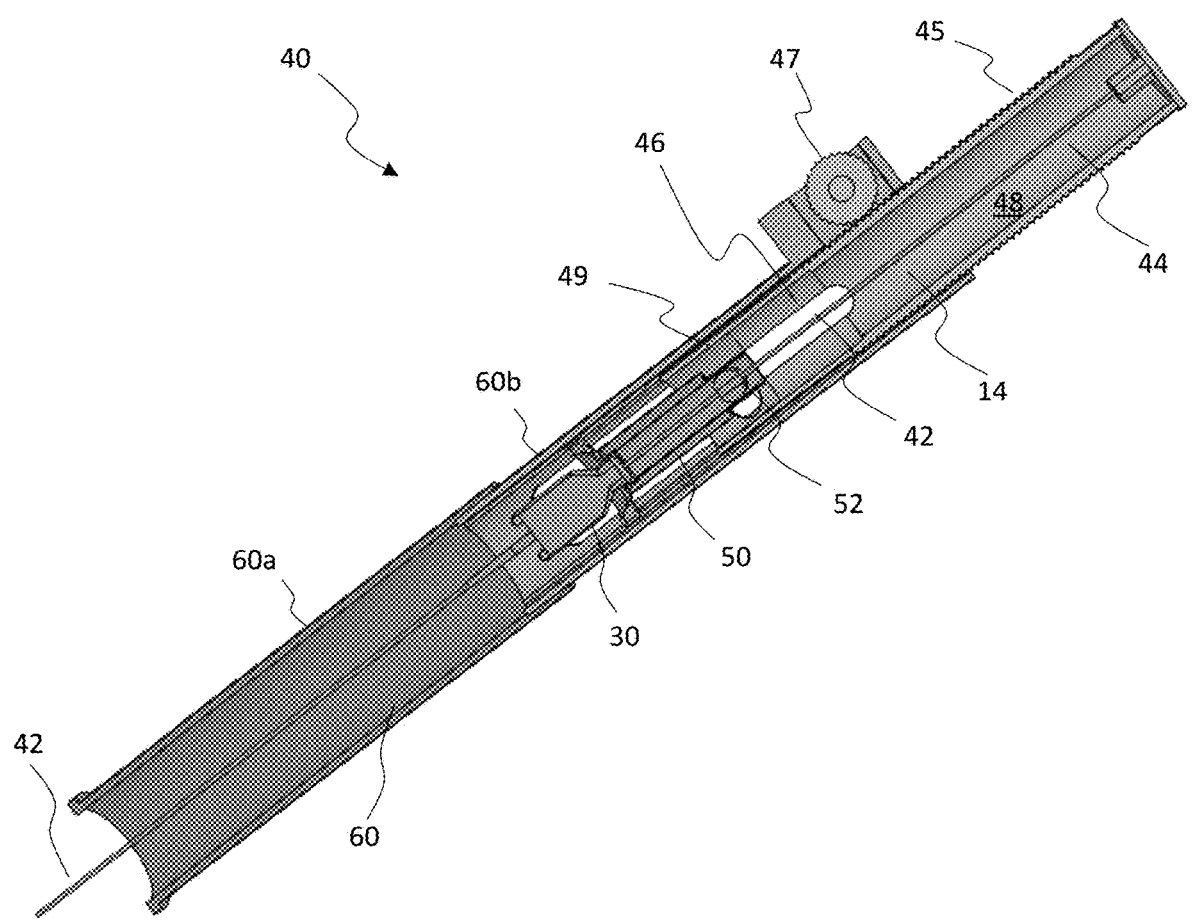
FIG. 7 is a cross-sectional view of an embodiment of the plug deployment device with the extractor having engaged a plug housing. The remaining portions of the coaxial needle assembly are not shown to reduce clutter.
Figure 8:
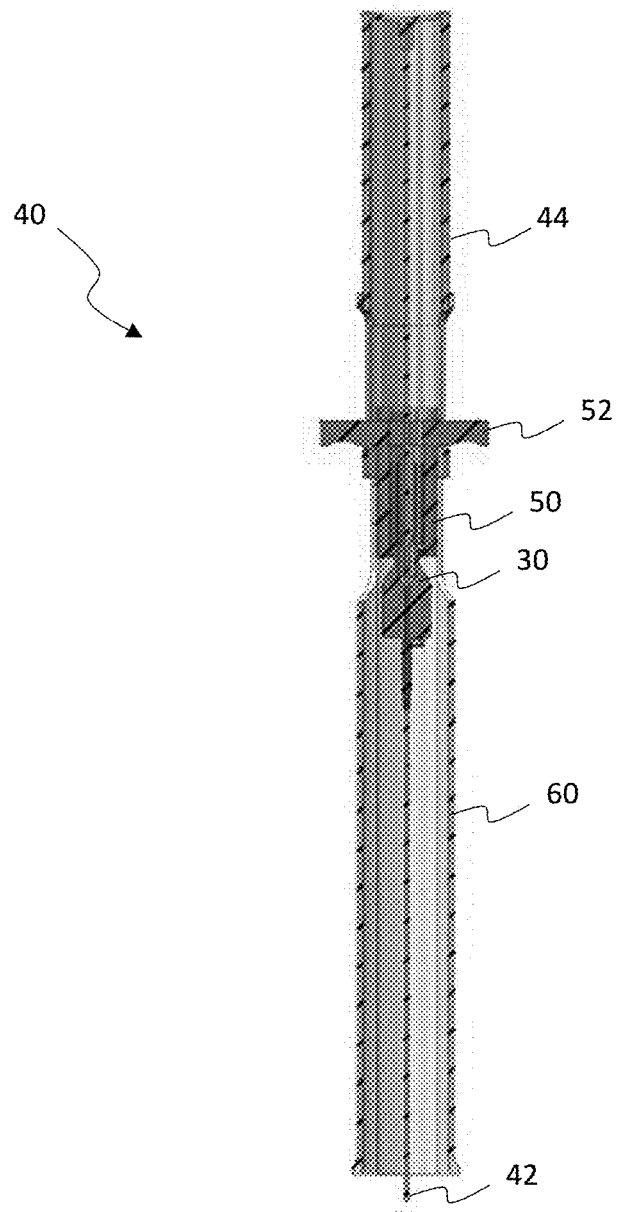
FIG. 8 is a cross-sectional elevation view of an embodiment of the plug deployment device with the extractor having engaged a plug housing. The remaining portions of the coaxial needle assembly are not shown to reduce clutter.
Figure 9:
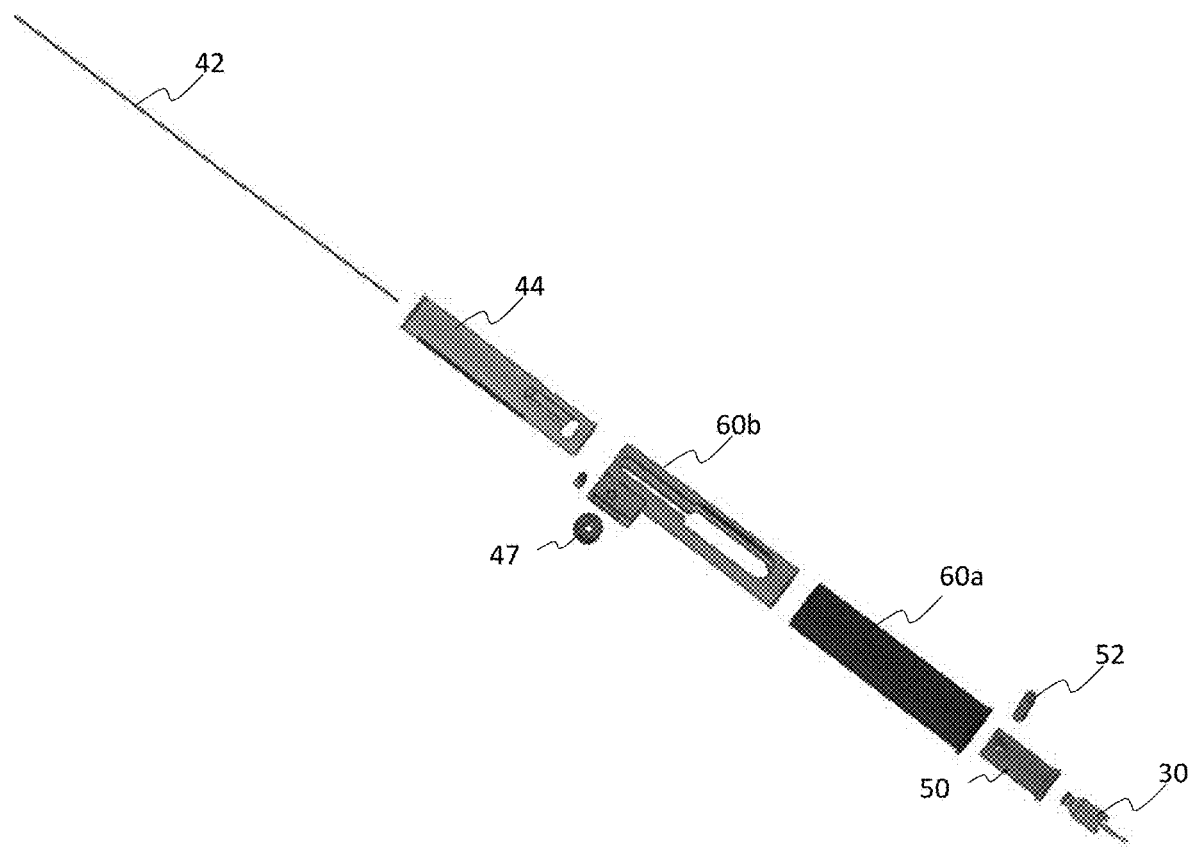
FIG. 9 is an exploded view of an embodiment of the plug deployment device.

An embodiment of plug deployment device 40 is depicted in FIGS. 5-10. Plug deployment device 40 includes plunger rod 42 having a fixed location relative to pusher component 44. In some embodiments, plunger 42 is secured to pusher component 44 as best depicted in FIGS. 6-8. As a result, plunger 42 and pusher component 44 move in a longitudinal direction as one.

Plunger 42 has a diameter sufficiently sized to pass through internal lumen 18 of coaxial needle 12 and the internal lumen of plug housing 30. In addition, plunger 42 is sufficiently rigid to move plug 28 under force to distal end 14 of coaxial needle 12.

In some embodiments, plunger 42 does not fully occupy lumen 18 of coaxial needle 12 because the outer diameter of plunger 42 is less than the diameter of lumen 18. Accordingly, a saline solution or other suitable substance, which may take the form of a liquid fluid, a powder, or other substance, may be introduced into coaxial needle lumen 18, from the trailing end thereof, so that it flows around plunger 42 and reaches the sealant plug. Such substance is selected to begin or accelerate hydration of the sealant plug. Thus, expansion of the sealant plug does not rely entirely on the presence of bodily fluid in the patient.

Plug deployment device 40 further includes support leg 60. Leading end 62 of support leg 60 is intended to reside in abutting relation to the patient's skin when plug deployment device 40 is moved into an operational position in which plunger 42 resides within coaxial needle 12 and coaxial needle 12 resides within internal lumen 41. Support leg 60 may be comprised of a multi-piece construction (60a and 60b) as shown in FIGS. 5-7 or a single piece construction as shown in FIG. 8. In some embodiments, the multi-piece construction is telescoping thereby allowing plug deployment device 40 to be used with coaxial needles of different lengths.

Support leg 60 is generally hollow to receive plunger 42, coaxial needle 12, and extractor 50. Some embodiments include window 64 to allow a user to visually confirm that extractor 50 has engaged coaxial needle 12 or plug housing 30. Moreover, support leg 60 includes one or more extraction channels 66 passing through its lateral surface 68. The depicted embodiment includes two extraction channels diametrically opposed from each other. However, the number of extraction channels and the relative locations of each can vary.

Pusher component 44 includes at least one extraction slot 46 passing through its lateral surface 48. The depicted embodiment includes two extraction slots diametrically opposed from each other. However, the number of extraction slots and the relative locations of each can vary.

Plug deployment device 40 preferably includes the same number of extraction channels 66 and extraction slots 46. In addition, extraction channels 66 and extraction slots 46 are axially aligned. However, the longitudinal length of extraction channels 66 are equal to or greater than the longitudinal length of extraction slots 46. The additional length of extraction channels 66 allows for longitudinal translation of pusher component 44, and its extraction slots 46 relative leg 60 and its extraction channels 66.

Both extraction channels 66 and extraction slots 46 are sized to receive extractor handles 52 and allow for longitudinal translation of extractor handles through extraction channels 66 and extraction slots 46. In some embodiments, the length of each extraction slot 46 is equal to or greater than the length of plug 28. In some embodiments, the length of each extraction slot 46 is equal to or greater than the amount of plug that remains in coaxial needle 12 when plunger 42 is fully inserted into coaxial needle 12. In some embodiments, the length of each extraction slot 46 is equal to or greater than the distance that extractor 50 must travel to cause plug 28 to exit coaxial needle 12. The relationship between the extractor and the deployment of plug 28 will be explained in subsequent paragraphs.

Pusher component 44 further includes locking passage 49, which is circumferentially offset from extraction slot 46. The depicted embodiment includes the combination of locking passage 49 and extraction slot 46 creating an L-shaped channel through which extractor handles 52 may travel. When extractor 50 is rotated to move extractor handles 52 into locking passage 49, extractor 50, pusher component 44, and plunger 42 will move as one when extractor handles 52 are translated in a longitudinal direction (see FIG. 10A). In contrast, when extractor 50 is rotated to move extractor handles 52 out of locking passage 49 and into extraction slot 46, extractor 50 can move relative to pusher component 44 and plunger 42 in a longitudinal direction. As depicted in FIG. 10B, a user can translate extractor handles 52 proximally through extraction slot 46 relative to pusher component 44. Ultimately, this functionality allows a user to extract coaxial needle 12, when connected to extractor 50, while pusher component 44 and plunger 42 remain in place.

In some embodiments, pusher component 44 includes ridges 45 configured to operably engage translation wheel 47 housed or connected to support leg 60. Translation wheel 47 allows the operator to modify the longitudinal location of pusher component 44, and in turn plunger 42, relative to support leg 60. Moreover, rotation of translation wheel 47 will cause longitudinal translation of extractor 50 when extractor 50 is rotated to move extractor handles 52 into locking passage 49. Some embodiments employ alternative known actuators/mechanisms to cause translation of pusher component 44 relative to support leg 60.

Figure 11:
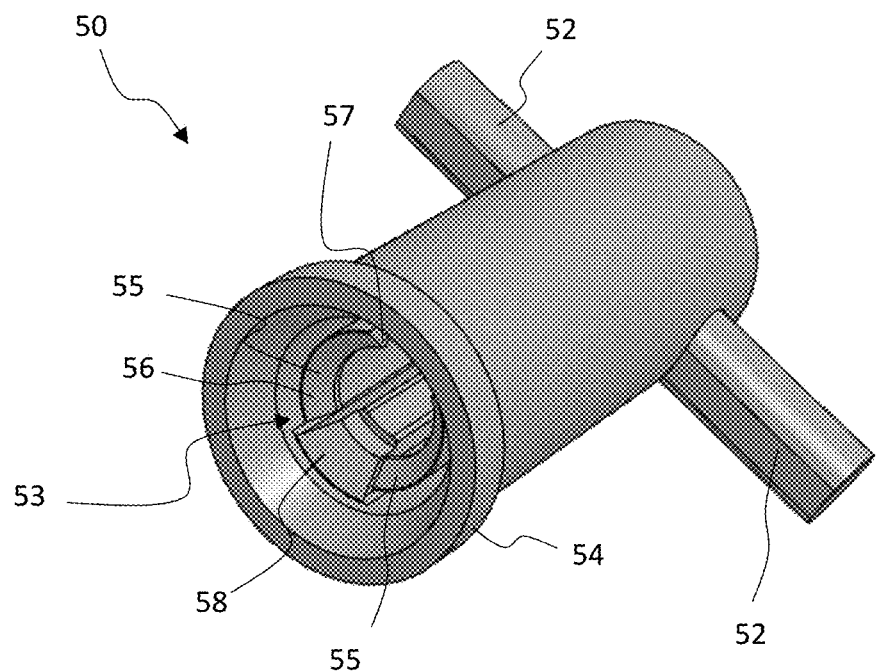
FIG. 11 is a perspective view of an embodiment of the extractor.
Figure 12:
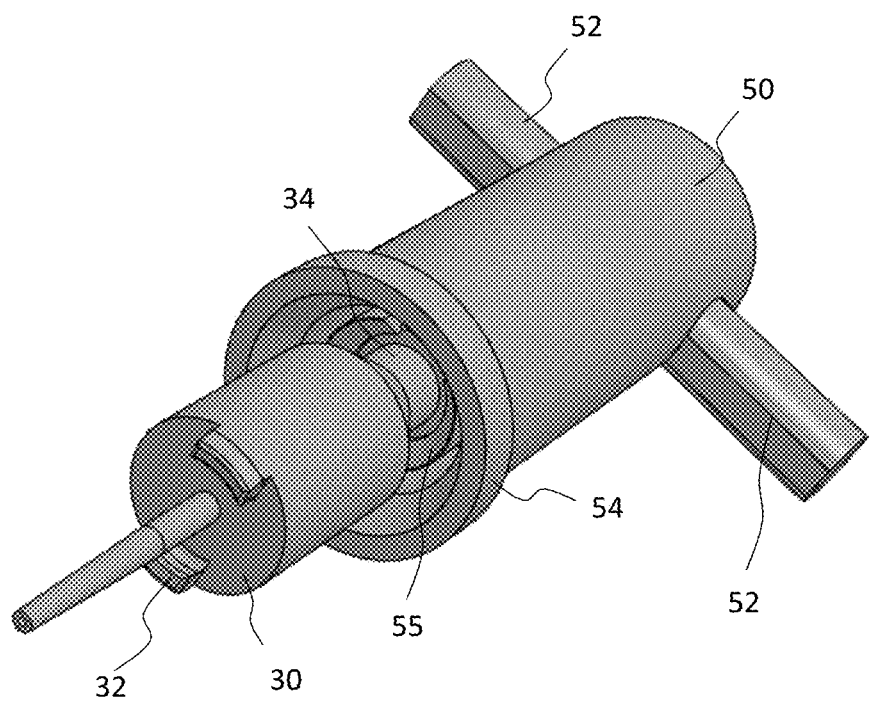
FIG. 12 is a perspective view of an embodiment of the extractor having engaged a proximal end of an embodiment of the plug housing.

As best depicted in FIGS. 11-12, extractor 50 includes female fitting 53 located at distal end 54. The depicted embodiment of female fitting 53 include a pair of diametrically opposed compliant clips 55. Compliant clips 55 each have tapered distal ends 56 which extend proximally to retention shelves 57. Compliant clips 55 flex outwardly in a radial direction when male fitting 34 is forced into tapered distal ends 56 until male fitting 34 extends proximally past tapered distal ends 56 and compliant clips 55 spring back into their respective positions of repose. Male fitting 34 is then secured within extractor 50 via shelves 57. The same functionality of female fitting 53 can be performed on luer connector 13 when plug housing 30 is not employed.

Some embodiments of extractor 50 include release sections 58 residing between compliant clips 55. A male fitting on plug housing 30 or on extractor 50 will have a correspondingly semi-annular flange configured to engage compliant clips 55 and rotate into release sections 58 thereby allowing male fitting 34 on plug housing 30 or on extractor 50 to be removed from extractor 50.

It should be noted that the location of the male and female fittings may be inverted. For example, the male fitting may reside on the extractor while the female fittings reside on the plug housing and/or luer connector. It should be noted that female fitting 53 and the male fitting on plug housing 30 or on extractor 50 may be alternative shapes or mechanisms configured to at least temporarily interconnect.

Extractor 50 further includes extractor handles 52. Extractor handles 52 extend laterally with respect to the longitudinal axis of extractor 50. Preferably, extractor handles 52 extend laterally a distance sufficient to allow a user to manipulate extractor handles 52. Alternatively, extractor handles 52 may connect to another exteriorly located structure manipulatable by a user.

The depicted embodiment shows two extractor handles 52, however, one or more handles may be used. In some embodiments, the number of extractor handles 52 coincides with the number of extraction slots 46 in pusher component 44. In some embodiments, the number of extractor handles 52 coincides with the number of extraction slots 46 in pusher component 44 and the number of extraction channels 66 in support leg 60.

As previously noted, plug deployment device 40 may be employed after coaxial needle 12 is moved, and preferably secured, at a plug deployment depth within the patient as exemplified in FIGS. 2-4. Coaxial needle 12 may be secured at the plug deployment depth using a stopper (e.g., stopper 11 in FIG. 2), spring clip, or any other known mechanism for preventing coaxial needle 12 form accidentally moving deeper within the patient.

After coaxial needle 12 is secured at the plug deployment depth, plug 28 is inserted into coaxial needle 12 or plug housing 30 is attached to coaxial needle 12. Plunger 42 is then inserted into internal lumen 18 of coaxial needle 12 and plug deployment device 40 is moved towards the patient to its operational location in which distal end 62 of support leg 60 is in contact with the patient's skin. While plug deployment device 40 is being moved to its operational location, internal lumen 41 of plug deployment device 40 translationally receives coaxial needle 12 and internal lumen 18 of coaxial needle 12 translationally receives plunger 42. Furthermore, plunger 42 pushes plug 28 towards distal end 14 of coaxial needle 12 while plug deployment device 40 is being moved to its operational location.

Figure 10A:
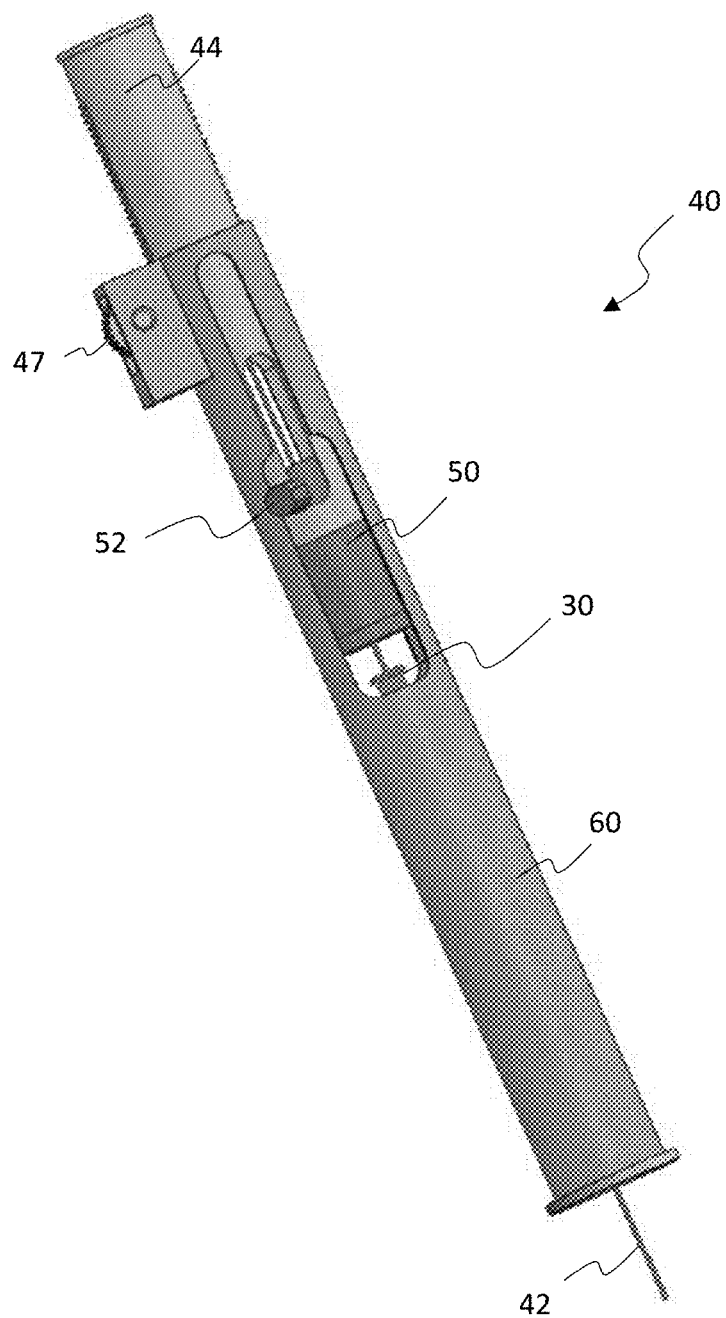
FIG. 10A is a perspective view of an embodiment of the plug deployment device during a step of translating the extractor towards the coaxial needle assembly.
Figure 10B:
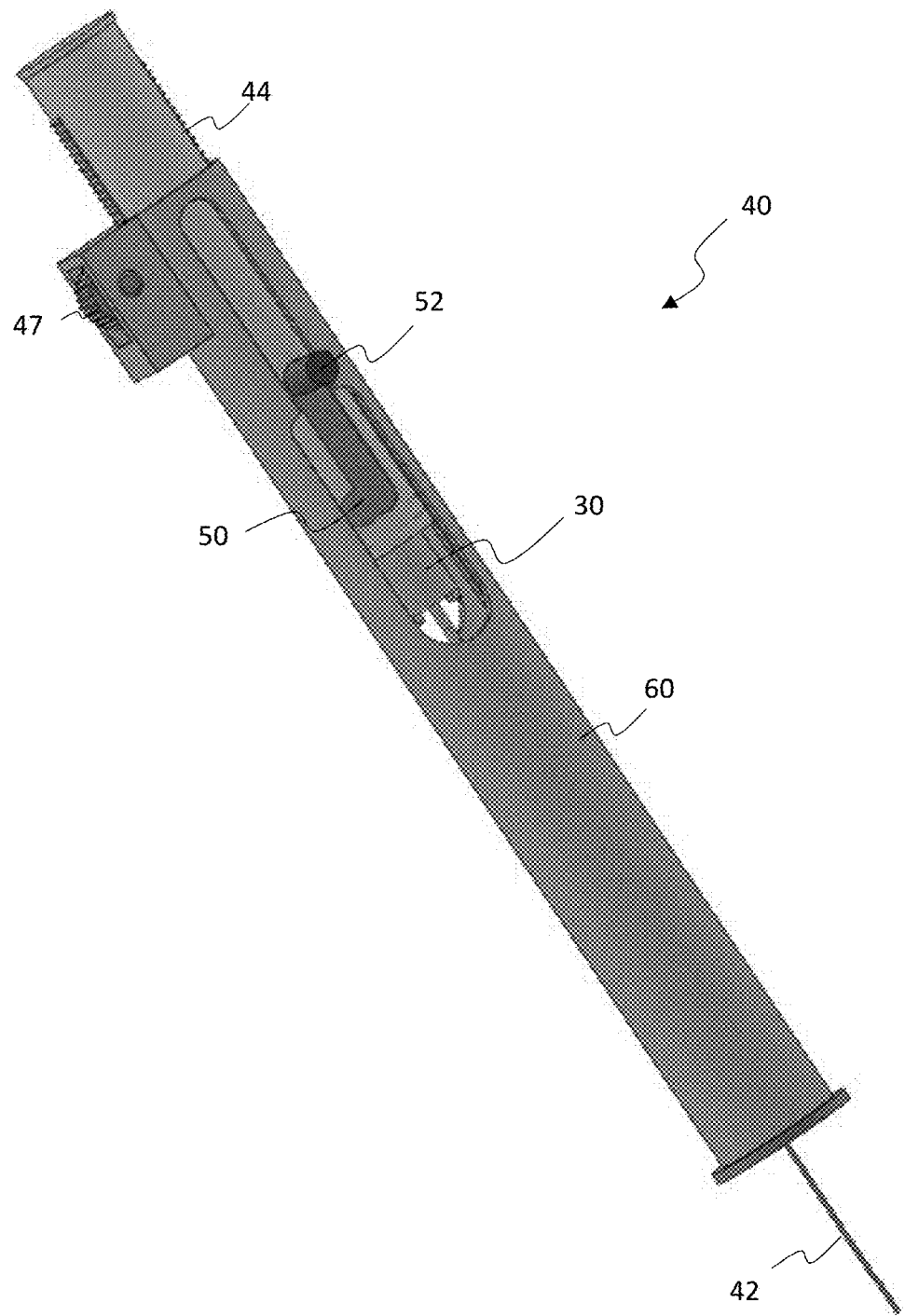
FIG. 10B is a perspective view of an embodiment of the plug deployment device during a step of extracting the coaxial needle assembly. This figure only depicts the plug housing from the coaxial needle assembly in an effort to reduce clutter. However, in practice the plug housing would be secured to the coaxial needle when the plug deployment device retracts the coaxial needle assembly.

Once plug deployment device 40 reaches its operational location and extractor handles 52 are rotated into locking passage 49, plug deployment device is in a translation configuration (see FIG. 10A). A user can then translate pusher component 44, and in turn extractor 50 and plunger 42, in a distal direction from an initial location. The initial location includes extractor 50 longitudinally spaced from the coaxial needle assembly, which may include luer connector 13 or plug housing 30. A user may control the translation by actuating roller 47 or any other mechanism known in the art that is configured to translate pusher component 44 relative to support leg 60.

Figure 13:
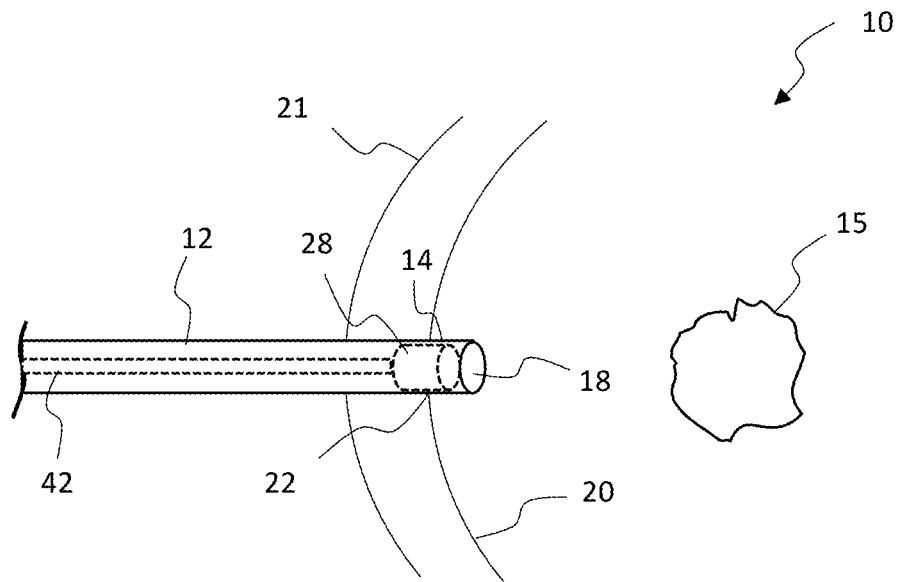
FIG. 13 is a diagram illustrating a coaxial needle secured at an exemplary plug deployment depth with a plug residing proximate to the distal end of the coaxial needle prior to deployment.

The user continues translating pusher component 44 until female fitting 53 of extractor 50 receives the male fitting of luer connector 13 or plug housing 30. At this point, plug deployment device 40 is in a needle engagement configuration and plunger 42 will have forced plug 28 to its insertion depth. The plug insertion depth includes at least a portion of plug 28 within internal lumen 18 of coaxial needle 12 as depicted in FIG. 13. Moreover, the plug insertion depth includes at least a portion of plug 28 residing within internal lumen 18 when coaxial needle 12 is retracted for the patient.

To ensure that plug 28 reaches its insertion depth when plug deployment device 40 is in a needle engagement configuration, plunger 42 and coaxial needle 12 both have predetermined lengths. The specific relative lengths between coaxial needle 12 and plunger 42 ensure that the plug will always be located at its insertion depth when extractor 50 connects to the coaxial needle assembly. It should be noted that the specific relative lengths between coaxial needle 12 and plunger 42 will be different depending on whether the coaxial needle assembly includes a plug housing. In any event, the specific relative lengths between coaxial needle 12 and plunger 42 are fixed to eliminate the possibility of human error associated with having to adjust the location of plunger 42 based on the depth of coaxial needle 12 within the patient.

In some embodiments, the length of the coaxial needle assembly, which includes coaxial needle 12, luer connector 13, and interconnected plug housing 30 if used, is greater than the length of an ensleevable section of plunger 42. The ensleevable section of plunger 42 includes the section between the distal end of plunger 42 and the female fitting in extractor 50 when plug deployment device 40 is in the needle engagement configuration. In other words, the ensleevable section of plunger 42 is the section of plunger 42 that is ensleeved by the coaxial needle assembly when plug deployment device 40 is in the needle engagement configuration.

In some embodiments, the length of the coaxial needle assembly is equal to the combined length of (1) plug 28 and (2) the ensleevable section of plunger 42. In some embodiments, the length of the coaxial needle assembly is equal to the combined length of (1) a predetermined sub length of plug 28 and (2) the ensleevable section of plunger 42. In some embodiments, the predetermined sub length of plug 28 is between 0.5 cm and 2 cm.

Figure 14:
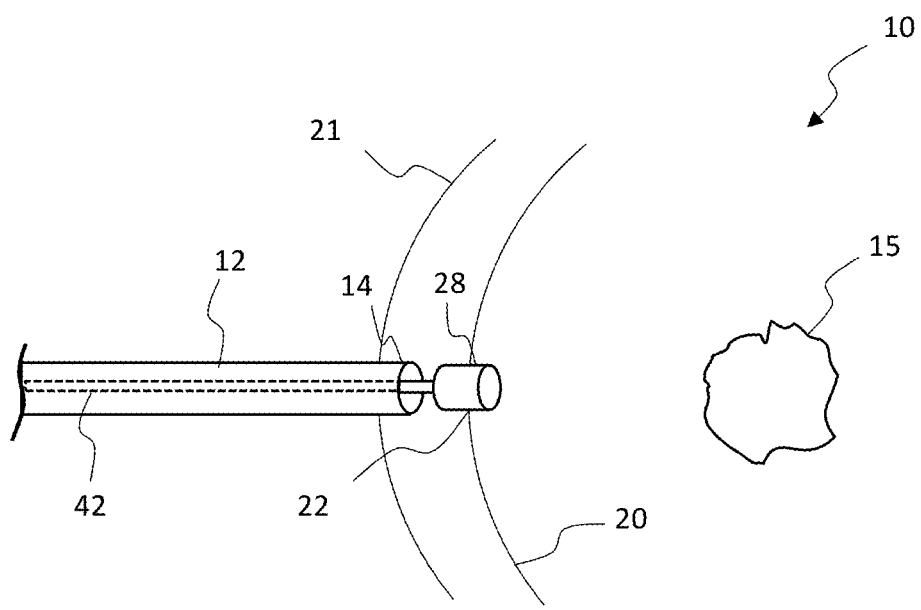
FIG. 14 is a diagram illustrating the plug deployed with a biopsy tract after partial retraction of the coaxial needle.

Once plug deployment device 40 is in the needle engagement configuration, a user can rotate extractor 50 to bring each extraction handle 52 out of its respective locking passage 49 an into longitudinal alignment with its respective extraction channel 66 and extraction slot 46. This configuration is referred to as the needle retraction configuration. When in the needle retraction configuration, the user can move extractor 50 in a proximal direction causing concurrent retraction of coaxial needle 12. However, plunger 42 remains stationary and holds plug 28 at its insertion location while coaxial needle is withdrawn from the patient. As a result, plug 28 is deployed at least partially within passage 22 as exemplified in FIG. 14.

Figure 15:
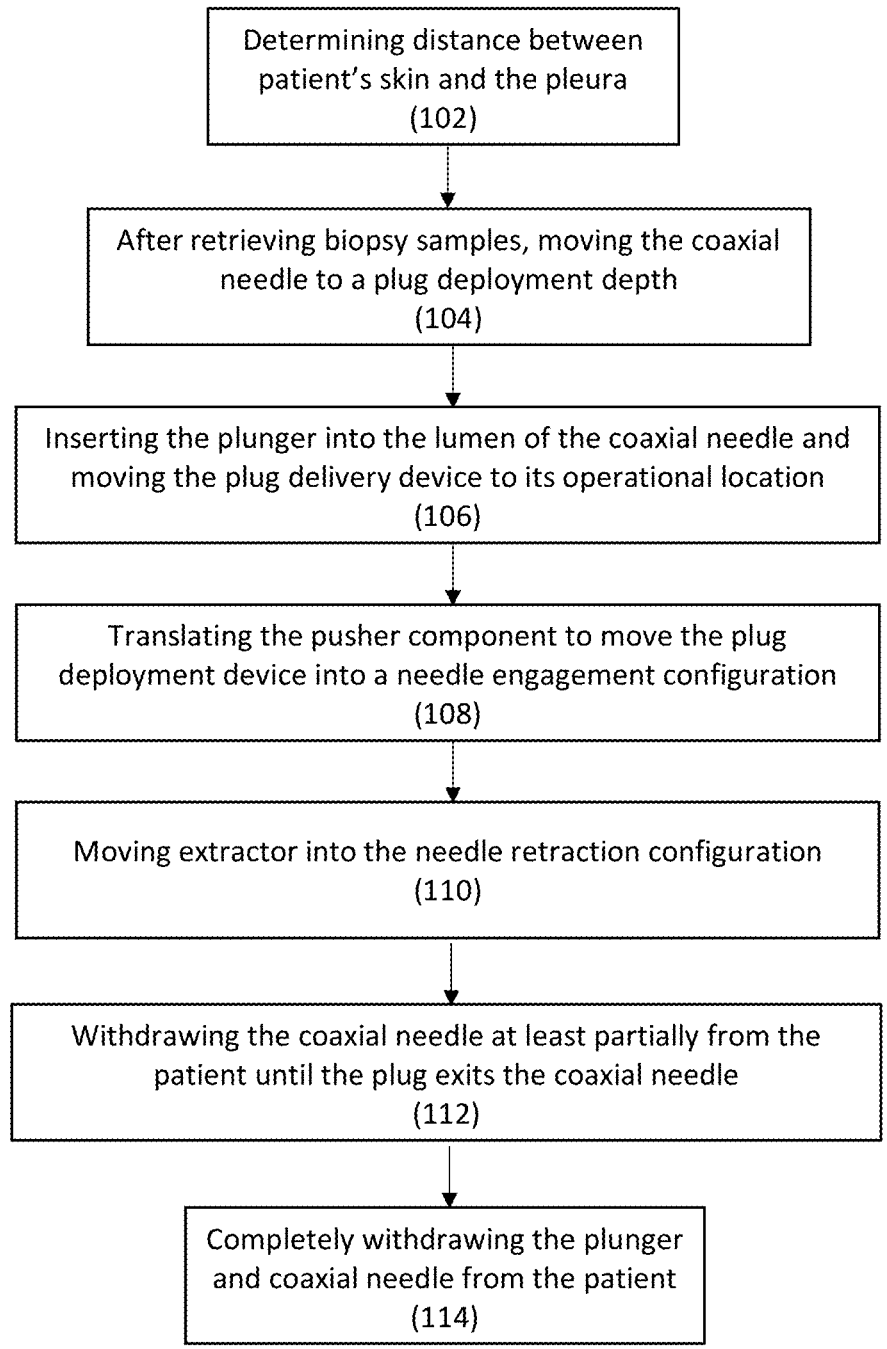
FIG. 15 is a flowchart of an embodiment of the novel method of the present invention.

The method of present invention for deploying a plug within a biopsy track in a pleura is exemplified in FIG. 15. As previously explained, the focus on a biopsy procedure in a lung is for exemplary purposes. The method of this invention is not restricted to sealing openings formed in lungs by biopsy procedures. Rather, it should be understood that this invention may be used to seal openings formed by any means in organs, such as the heart, brain, liver, spinal cord, and kidneys, and even in hard tissue such as bone, cartilage, and the like.

As provided in FIG. 15, at step 102 a user, typically a surgeon, determines the distance between a patient's skin and pleura. Determining the distance may be accomplished by any method known to a person of ordinary skill in the art, including but not limited to, acquiring one or more medical images of the surgical site. The medical images may be acquired by any imaging devices, including, but not limited to fluoroscopy, ultrasound, X-ray, magnetic resonance imaging, computed axial tomography (CAT) scanning, and other imaging techniques.

Following the retrieval of biopsy samples, the coaxial needle is moved to a plug deployment depth at step 104. In some embodiments, the coaxial needle will be secured at the plug deployment depth using methods and devices known in the art.

At this point, a plug is inserted into the coaxial needle or a plug housing is connected to the coaxial needle. A user can then perform the following steps using any of the various embodiments of the plug deliver device described herein.

At step 106, a user can insert the plunger of the plug delivery device into the lumen of the coaxial needle and move the plug delivery device to its operational location, in which the distal end of the support leg or distal most end of the plug delivery device is adjacent to the patient's skin. In some embodiments, the extractor handles are first moved into the locking channels in the pusher component prior to moving the plug delivery device to its operational location. However, the extractor handles may be moved into the locking channels prior to moving the drug delivery device to its needle engagement configuration.

Once the plug delivery device reaches its operational location, a user can longitudinally translate the pusher component in a distal direction to move the plug deployment device into a needle engagement configuration at step 108. Then, at step 110, a user can move the extractor into the needle retraction configuration. From there, a user can withdraw the coaxial needle at least partially from the patient until the plug exits the coaxial needle at step 112. Finally, at step 114, a user can completely withdraw the plunger and coaxial needle from the patient.

Shortly after implantation and after having been in contact with moisture, or another predetermined stimulant, plug 28 expands to seal passage 22 preventing air from escaping the lungs. In other applications, the plug is used to stop bleeding or other liquid fluid flow from the liver, heart, thecal sac, etc.

Some embodiments include discharging a coagulating agent proximate to the biopsy tract prior to deploying the expandable plug similar to the method and system disclosed in U.S. patent application Ser. No. 17/200,242 by the same inventors, which is incorporated herein by reference. Similar to the '242 application, some embodiments of the coagulating agent in the present invention are aqueous solutions, and the expandable plug is comprised of a non-liquid or non-fluid material but may be configured to absorb an aqueous solution. In other words, the coagulating agent is fluidic in nature with an ability to flow as a fluid and no fixed shape prior to coagulation. In contrast, the expandable plug has a definable shape and while some embodiments can absorb fluids, the plug itself has a gel-like, semisolid, or solid state.

In some embodiments, the coagulating agent is the patient's blood, which may have been retrieved prior to or during the surgical procedure. The patient's blood is highly advantageous as a peripheral sealant because it is safe to the patient with no risk of the patient having an allergic or adverse reaction to their own blood. In addition, since blood is 90% water and is located in close contact to the desiccated or partially desiccated plug, the blood will act as a source for the high concentration of water immediately abutting the desiccated hydrogel plug to move via osmosis into the desiccated plug and could enhance the speed at which the plug expands to fill the void of the biopsy tract more rapidly. As a result, the use of blood further reduces the sealing time of the plug in comparison with other coagulating agents.

In some embodiments, the coagulating agent is a blood clot derived from the patient. Moreover, the coagulating agent may be comprised of or include an adhesive or a coagulation catalyst. In some embodiments, the coagulating agent is any agent known to a person of ordinary skill in the art that is biocompatible and adapted to transition from a liquid to a gel-like, semisolid state, or solid state. Some examples include but are not limited hyaluronic acid, moisture sensitive curing hydrogel, two-part curing hydrogel, and adhesive.

Some embodiments include a step of inserting the coagulating agent after the plug has been delivered. Some embodiments include inserting coagulating agent before and after the plug is delivered.

Some embodiments in which a coagulating agent is deployed include coaxial needle 12 having one or more coagulating agent discharge ports located in the lateral wall of coaxial needle 12. In such instances, the preferred plug deployment depth of coaxial needle 12 includes the discharge ports located within roughly 2 cm from the organ wall. In some embodiments, the preferred depth of coaxial needle 12 includes the discharge ports located between roughly 1 cm and 2 cm from organ wall 20.

Some embodiments of the coaxial needle that include laterally disposed discharge ports also include a seal or membrane distally located from the discharge ports. The membrane is configured to seal the aperture in the distal end of the coaxial needle to ensure that the coagulating agent exits the discharge ports rather than the aperture in the distal end of the coaxial needle. The membrane is further configured to open in response to an actuator or in response to a needle or other surgical instrument applying a force to the internal/proximal surface of the membrane.

Some embodiments of the membrane include a plurality of triangular shaped flaps with the vertices of the triangles meeting generally in the middle of the membrane. A needle can be forced through the meeting point of the vertices and the triangular sections of the membrane give way to the advancing needle. In some embodiments, the flaps are of a different shape so long as they collectively act to seal the lumen of the coaxial needle. In some embodiments, the flaps are made of a flexible material. In addition, the flaps are preferably in overlapping or in a sealable relationship with each other when not subject to the external force of a needle or surgical instrument.

In some embodiments, the plug is pre-hydrated prior to insertion into the patient. The pre-hydration reduces the time necessary for the plug to reach its maximum expansion. In some embodiments, the plug is pre-hydrated to 25% of its maximum expansion. In some embodiments, the plug is pre-hydrated to between 10% and 30% of its maximum expansion. In some embodiments the plug is pre-hydrated for roughly 5 minutes. In some embodiments the plug is pre-hydrated for roughly 3 minutes to 10 minutes.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A sealant plug delivery system, comprising:
   a coaxial needle assembly having an internal lumen for delivering a sealant plug within a patient;
   a plug delivery device, the plug delivery device including:
      a support leg, the support leg having:
         a proximal end, a distal end, and an elongated body extending therebetween;
         a receiving space configured to receive the coaxial needle assembly;
      a plunger rod extending at least partially through the receiving space of the support leg, the plunger rod further including:
         a cross-sectional area smaller than a cross-sectional area of the internal lumen of the coaxial needle assembly;
         a longitudinally adjustable relation with respect to the support leg;
      an extractor configured to translate in a longitudinal direction with respect to the support leg, the extractor further including:
         a locked configuration in which the extractor moves concurrently with the plunger rod in the longitudinal direction;
         an unlocked position in which the extractor is configured to move relative to the plunger rod in the longitudinal direction;
         a needle connection component configured to engage the coaxial needle assembly;
      whereby the extractor configured to move distally in the longitudinal direction to engage the coaxial needle assembly and, while in the unlocked position, the extractor configured to translationally retract to concurrently retract the coaxial needle assembly without moving the plunger rod to deploy the sealant plug residing in the coaxial needle assembly.

2. The sealant plug delivery system of claim 1, further including the coaxial needle assembly having a length that is equal to or greater than a distance between the distal end of the plunger rod and the needle connection component of the extractor when the extractor is in the locked configuration.

3. The sealant plug delivery system of claim 1, further including the coaxial needle assembly having a first length that is equal to or greater than an ensleeved section of the plunger rod when the extractor is connected to the coaxial needle assembly.

4. The sealant plug delivery system of claim 1, further including an extraction handle in operable communication with the extractor, whereby actuation of the extraction handle causes the extractor to translate at least when the extractor is in the unlocked position.

5. The sealant plug delivery system of claim 4, further including an extraction slot disposed in a lateral surface of the support leg, wherein the extraction slot has a length extending in a longitudinal direction and is configured to receive the extraction handle.

6. The sealant plug delivery system of claim 5, further including a pusher component configured to translate in the longitudinal direction relative to the support leg, the pusher component including:
   a lumen configured to receive the extractor;
   an extraction channel laterally aligned with the extraction slot in the support leg, wherein the extraction channel extends in the longitudinal direction and is configured to receive the extraction handle; and
   a locking passage into which the extraction handle configured to be rotated to move the extractor into the locked position.

7. The sealant plug delivery system of claim 6, further including a translation actuator configured to translate the pusher component when actuated.

8. The sealant plug delivery system of claim 1, wherein the coaxial needle assembly includes a plug housing in which the sealant plug initially resides prior to the plunger rod forcing the sealant plug towards the distal end of the coaxial needle.

9. A sealant plug delivery system, comprising:
   a plug delivery device, the plug delivery device including:
   a support leg, the support leg having:
      a proximal end, a distal end, and an elongated body extending therebetween;
      an internal receiving space configured to receive an implanted coaxial needle assembly through an opening in the distal end;
   a plunger rod extending at least partially through the internal receiving space of the support leg, the plunger rod further including:
      a cross-sectional area smaller than a cross-sectional area of the internal lumen of the implanted coaxial needle assembly;
      a longitudinally adjustable relation with respect to the support leg;
   an extractor configured to translate in a longitudinal direction with respect to the support leg, the extractor further including:
      a locked configuration in which the extractor moves concurrently with the plunger rod in the longitudinal direction;
      an unlocked position in which the extractor is configured to move relative to the plunger rod in the longitudinal direction;
      a needle connection component configured to engage the implanted coaxial needle assembly;
   whereby the extractor configured to move distally in the longitudinal direction to engage the implanted coaxial needle assembly and, while in the unlocked position, the extractor configured to translationally retract to concurrently retract the implanted coaxial needle assembly without moving the plunger rod to deploy a sealant plug residing in the coaxial needle assembly.

10. The sealant plug delivery system of claim 9, further including a coaxial needle assembly having an internal lumen for delivering an expandable, biocompatible sealant plug within a patient.

11. The sealant plug delivery system of claim 10, further including the coaxial needle assembly having a length that is equal to or greater than a distance between the distal end of the plunger rod and the needle connection component of the extractor when the extractor is in the locked configuration.

12. The sealant plug delivery system of claim 10, further including the coaxial needle assembly having a first length that is equal to or greater than an ensleeved section of the plunger rod when the extractor is connected to the coaxial needle assembly.

13. The sealant plug delivery system of claim 9, further including an extraction handle in operable communication the extractor, whereby actuation of the extraction handle causes the extractor to translate at least when the extractor is in the unlocked position.

14. The sealant plug delivery system of claim 13, further including an extraction slot disposed in a lateral surface of the support leg, wherein the extraction slot has a length extending in a longitudinal direction and is configured to receive the extraction handle.

15. The sealant plug delivery system of claim 14, further including a pusher component configured to translate in the longitudinal direction relative to the support leg, the pusher component including:
   a lumen configured to receive the extractor;
   an extraction channel laterally aligned with the extraction slot in the support leg, wherein the extraction channel extends in the longitudinal direction and is configured to receive the extraction handle; and
   a locking passage into which the extraction handle configured to be rotated to move the extractor into the locked position.

16. The sealant plug delivery system of claim 15, further including a translation actuator configured to translate the pusher component when actuated.

17. A sealant plug delivery system, comprising:
   a coaxial needle assembly having an internal lumen for delivering a sealant plug within a patient;
   a plug delivery device, the plug delivery device including:
   a support leg, the support leg having:
      a proximal end, a distal end, and an elongated body extending therebetween;
      an internal receiving space configured to receive the coaxial needle assembly through an opening in the distal end;
   a plunger rod extending at least partially through the internal receiving space of the support leg, the plunger rod further including:
      a cross-sectional area smaller than a cross-sectional area of the internal lumen of the coaxial needle assembly;
      a longitudinally adjustable relation with respect to the support leg;
   an extractor configured to translate in a longitudinal direction with respect to the support leg, the extractor further including:
      a locked configuration in which the extractor moves concurrently with the plunger rod in the longitudinal direction;
      an unlocked position in which the extractor is configured to move relative to the plunger rod in the longitudinal direction;
      a needle connection component configured to engage the coaxial needle assembly;
   the coaxial needle assembly having a length that is equal to or greater than a distance between the distal end of the plunger rod and the needle connection component of the extractor when the extractor is in the locked configuration;

whereby the extractor configured to move distally in the longitudinal direction to engage the coaxial needle assembly and, while in the unlocked position, the extractor configured to translationally retract to concurrently retract the coaxial needle assembly without moving the plunger rod to deploy the sealant plug residing in the coaxial needle assembly.

18. The sealant plug delivery system of claim 17, wherein the length of the coaxial needle assembly is equal to or greater than an ensleeved section of the plunger rod when the extractor is connected to the coaxial needle assembly.

19. The sealant plug delivery system of claim 17, further including an extraction handle in operable communication the extractor, whereby translation of the extraction handle causes the extractor to translate at least when the extractor is in the unlocked position.

20. The sealant plug delivery system of claim 19, further including an extraction slot disposed in a lateral surface of the support leg, wherein the extraction slot has a length extending in a longitudinal direction and is configured to receive the extraction handle.

\* \* \* \* \*